(12) United States Patent
Feifer et al.

(10) Patent No.: US 8,691,798 B2
(45) Date of Patent: Apr. 8, 2014

(54) SYNTHESIS OF 2,4-PYRIMIDINEDIAMINES

(71) Applicant: Rigel Pharmaceuticals, Inc., South San Francisco, CA (US)

(72) Inventors: Ulfried Feifer, Linz (AT); Karl-Heinz Giselbrecht, Langholzfeld (AT); Michael Wolberg, Neutraubling (DE)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/912,856

(22) Filed: Jun. 7, 2013

(65) Prior Publication Data
US 2013/0274499 A1 Oct. 17, 2013

Related U.S. Application Data

(62) Division of application No. 13/625,552, filed on Sep. 24, 2012, now Pat. No. 8,481,724, which is a division of application No. 12/829,126, filed on Jul. 1, 2010, now Pat. No. 8,299,242.

(60) Provisional application No. 61/270,073, filed on Jul. 2, 2009.

(51) Int. Cl.
*C07F 9/09* (2006.01)
(52) U.S. Cl.
USPC .......................................... 514/136; 558/203

(58) Field of Classification Search
USPC ......................................................... 514/136
See application file for complete search history.

(56) References Cited

U.S. PATENT DOCUMENTS

| 8,163,902 B2 | 4/2012 | Bhamidipati et al. |
| 2009/0114877 A1* | 5/2009 | Negi et al. ................ 252/182.29 |
| 2011/0003986 A1 | 1/2011 | Felfer et al. |

FOREIGN PATENT DOCUMENTS

| WO | 2006/078846 | 7/2006 |
| WO | 2008/064274 | 5/2008 |

OTHER PUBLICATIONS

Antii et al. Tetrahedron Letters 43 (2002) 3793-3794.*
Oslob et al., "Water-soluble prodrugs of an Aurora kinase inhibitor", Bioorganic & Medicinal Chemistry Letters, 19(5), 2009, 1409-1412, XP025994282.
Chassaing et al., "Highly water-soluble prodrugs of anthelmintic benzimidazole carbamates: synthesis, pharmacodynamics, and pharmacokinetics", Journal of Medicinal Chemistry, 51(5), 2008, 1111-1114, XP009135085.

* cited by examiner

*Primary Examiner* — Kahsay Habte
(74) *Attorney, Agent, or Firm* — Travis Young; McDonnell Boehnen Hulbert & Berghoff LLP

(57) ABSTRACT

Disclosed herein are methods for synthesizing 2,4-pyrimidinediamines as well as intermediates used therein.

4 Claims, 2 Drawing Sheets

US 8,691,798 B2
// 1

SYNTHESIS OF 2,4-PYRIMIDINEDIAMINES

CROSS-REFERENCE TO RELATED APPLICATIONS

This application is a divisional of U.S. application Ser. No. 13/625,552, filed Sep. 24, 2012, which is a divisional of U.S. application Ser. No. 12/829,126, filed Jul. 1, 2010 now U.S. Pat. No. 8,299,242, issued Oct. 30, 2012, which claims the benefit of U.S. Provisional Application Ser. No. 61/270,073, filed Jul. 2, 2009, which are hereby incorporated by reference in their entirety.

I. BACKGROUND OF THE INVENTION

1. Field of the Invention

This invention relates to the field of pharmaceutical/process chemistry. Disclosed herein are methods for synthesizing 2,4-pyrimidinediamines as well as intermediates used therein. As an embodiment, provided herein is a process for preparing N4-(2,2-dimethyl-4-[(dihydrogen phosphonoxy) methyl]-3-oxo-5-pyrido[1,4]oxazin-6-yl)-5-fluoro-N2-(3,4, 5-trimethoxyphenyl)-2,4-pyrimidinediamine disodium salt (compound of formula I), particularly hydrates (such as a hexahydrate) of the compound of formula I, a 2,4-pyrimidinediamine that is useful in the treatment and prevention of various diseases.

2. Summary of the Related Art

Various-classes of 2,4-pyrimidinediamine compounds have been discovered that have myriad therapeutic uses. See, for example, U.S. application Ser. No. 10/355,543 filed Jan. 31, 2003 (U.S. 2004/0029902A1), international application Ser. No. PCT/U.S.03/03022 filed Jan. 31, 2003 (WO 03/063794), U.S. application Ser. No. 10/631,029 filed Jul. 29, 2003 (U.S.2007/0060603), international application Ser. No. PCT/U.S.03/24087 (WO 2004/014382), U.S. application Ser. No. 10/903,263 filed Jul. 30, 2004 (U.S.2005/0234049), and international application Ser. No. PCT/U.S.2004/24716 (WO/2005/016893). Each of these applications is incorporated by reference in its entirety.

One of the process for preparing the 2,4-pyrimidinediamine compounds is described in U.S. application Ser. No. 11/539,074, filed Oct. 5, 2006, which is incorporated herein by reference in its entirety in the present disclosure.

II. SUMMARY OF THE INVENTION

The invention comprises a processes for preparing N4-(2, 2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine disodium salt (compound of formula I):

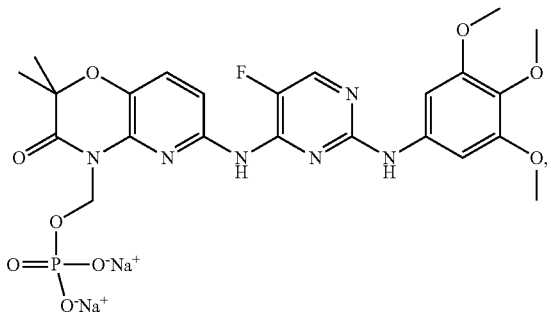

I as well as hydrates (such as a hexahydrate) thereof. The compound of formula I (and hydrates thereof) is a 2,4-pyrimidinediamine that is useful in the treatment and prevention of various diseases. The invention further comprises solvate intermediates useful in the process as well as the compound produced by the process.

It will be appreciated by one of skill in the art that the embodiments summarized above may be used together in any suitable combination to generate embodiments not expressly recited above and that such embodiments are considered to be part of the present invention.

III. BRIEF DESCRIPTION OF THE FIGURES

IV. DETAILED DESCRIPTION OF THE INVENTION

1. Definitions

Figure 1:
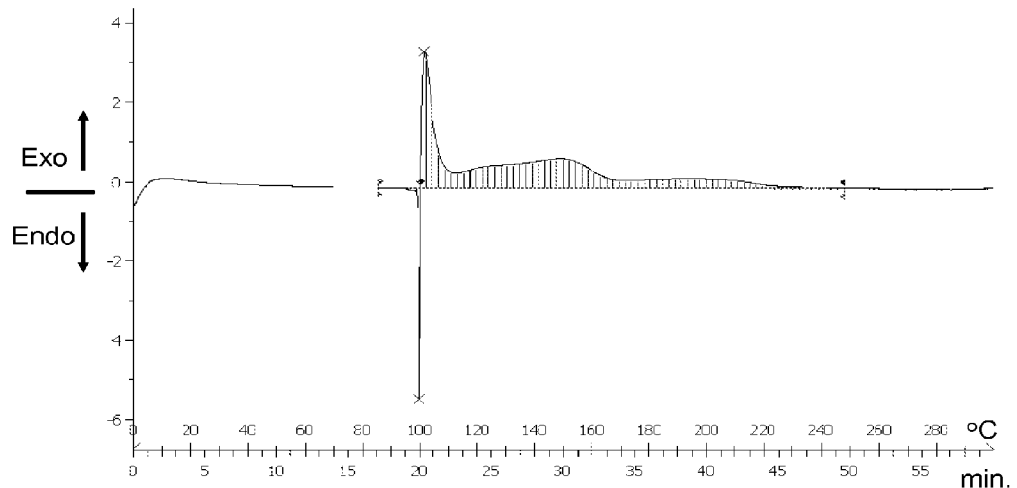
FIG. 1 illustrates a dynamic differential scanning calorimetry experiment (DSC) in closed cup of neat di-tert-butylchloromethyl phosphate (3.834 mg).

As used herein, the following definitions shall apply unless otherwise indicated.

Unless defined otherwise, all technical, and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

"Amide" refers to the group $R^{20}CON(R^{21})_2$ wherein $R^{20}$ is selected from hydrogen or optionally substituted alkyl; and each $R^{21}$ is independently hydrogen or optionally substituted alkyl, or both of $R^{21}$ and the nitrogen with which they are attached form a 4 to 6 membered aliphatic ring; or $R^{20}$ and one of the $R^{21}$ join together with the carbon and nitrogen to which they are attached, respectively, combine to form a 4 to 6 membered nitrogen containing ring, and the other $R^{21}$ is hydrogen or optionally substituted alkyl. Amides include primary amides, secondary amides (such as, but not limited to, alkyl formamides and acetamides, such as N-methyl acetamide), and tertiary amides (such as, but not limited to, N,N-dialkylacetamides, N,N-dialkylformamides, N-alkylpyrrolidones, and N-alkylpiperidones). Particular examples of tertiary amides suitable for use in the presently disclosed solvates include, without limitation N,N-dimethylacetamide, N,N-dimethylformamide, N-methylpyrrolidinone, N-methylpiperidinone.

"Alkyl" refers to monovalent saturated aliphatic hydrocarbyl groups having from 1 to 8 carbon atoms, such as, 1 to 6 carbon atoms or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—). Also by way of example, a methyl group, an ethyl group, an n-propyl, an isopropyl group, a n-butyl group, an isobutyl group, sec-butyl group, and t-butyl are all represented by the term C$_1$-C$_4$ alkyl. Likewise terms indicating larger numerical ranges of carbon atoms are representative of any linear or branched hydrocarbyl falling within the numerical range. This inclusiveness applies to other hydrocarbyl terms bearing such numerical ranges.

"Base" refers to substance that can accept protons. Examples of bases include, but are not limited to, carbonates, such as cesium carbonate, sodium carbonate, sodium bicarbonate, potassium carbonate, hydroxides, such as, sodium hydroxide, potassium hydroxide, lithium hydroxide, and ammonia.

"Halo" or "halogen" refers to fluoro, chloro, bromo, and iodo.

"Solvate" refers to a complex formed by combination of at least one solvent molecule with at least one molecule or ion of the solute. One of ordinary skill in the art will appreciate that the stoichiometry of the solvent to the solute in a solvated may be greater than one, equal to one or less than one. The solvent can be an organic compound, an inorganic compound, or a mixture of both. Some examples of solvents include, but are not limited to, methanol, acetic acid, N,N-dimethylformamide, tetrahydrofuran, dimethylsulfoxide, and water. When used herein, the term "solvate" is not intended to restrict the solvate compounds described herein to any particular sort of bonding (such as ionic or coordinate covalent bonds).

The term "substituted," when used to modify a specified group or radical, means that one or more hydrogen atoms of the specified group or radical are each, independently of one another, replaced with the same or different substituent groups as defined below.

Substituent groups on optionally substituted alkyls are alkyl, halo, haloalkyl, nitroso, and cyano.

Similarly, it is understood that the above definitions are not intended to include impermissible substitution patterns (such as carbon substituted with five groups, i.e., pentavalent carbon). Such impermissible substitution patterns are easily recognized by a person having ordinary skill in the art.

2. Compositions and Process

Disclosed herein are methods for synthesizing 2,4-pyrimidinediamines as well as intermediates used therein. As an embodiment, provided herein is a process for preparing N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine disodium salt (Compound of formula I) (including hydrates thereof, particularly a hexahydrate), a 2,4-pyrimidinediamine that is useful in the treatment and prevention of various diseases.

The compound of formula I has been described in U.S. Pat. No. 7,449,458, filed Jan. 19, 2006, which is incorporated herein by reference in its entirety in the present disclosure. The phosphate containing progroups such as in the compounds of formulae I, II, III, and VI may increase the solubility of the 2,4-pyrimidinediamine compounds that exhibit poor solubility under physiological conditions (for example, solubilities of less than about 10 µg/mL). The phosphate-containing progroups may aid the solubility of the underlying active 2,4-pyrimidinediamine compound, which in turn may increase its bioavailability when administered orally. The phosphate progroups may be metabolized by phosphatase enzymes found in the digestive tract, permitting uptake of the underlying active drug.

The U.S. Pat. No. 7,449,458, filed Jan. 19, 2006, discloses that the water solubility and oral bioavailability of a particular biologically active 2,4-pyrimidinediamine compound, such as compound of formula IV:

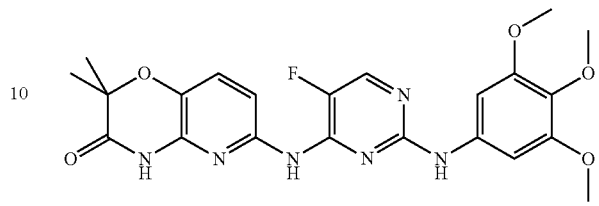

IV increased dramatically when formulated to include a pro-group at the ring nitrogen atom as in compound of formula II:

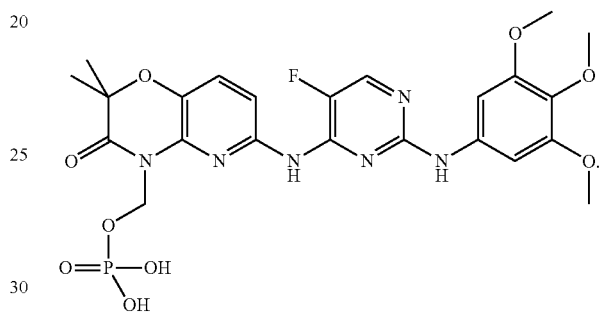

II

Where the water solubility of the compound of formula IV was found to be in the range of about 1-2 µg/mL in aqueous buffer under physiological conditions, the solubility of the corresponding phosphate prodrug (compound of formula II) was found to be greater than 5 mg/mL under the same conditions, or approximately 2000 times greater. This increased water-solubility allows for better dissolution in the gut, thereby facilitating oral administration.

A process for preparing the compound of formula I has been described in U.S. application Ser. No. 11/539,074, filed Oct. 5, 2006, which is incorporated herein by reference in its entirety in the present disclosure.

In a broad aspect, the invention is directed to a process for making an amide solvate of a compound of formula II (below) (formula IIa) and converting it into the compound of formula I. In a more specific sense, the invention is directed to a process where an acid solvate of the compound of formula II is converted to an amide solvate, and the amide solvate converted to the compound of formula I. In a more specific embodiment, the invention is directed to a process for preparing a compound of formula I:

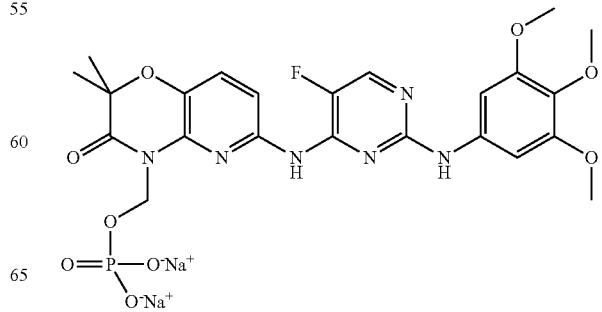

I comprising:

a) contacting an acid solvate of a compound of formula II:

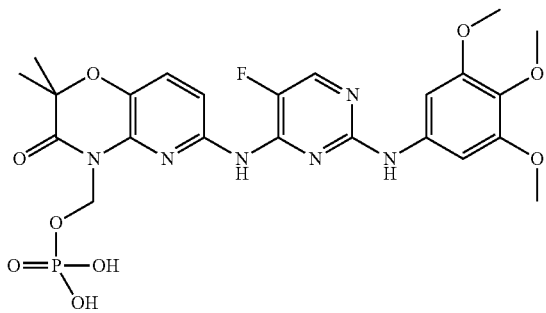

with an amide under conditions suitable for forming an amide solvate of the compound of formula II; and b) contacting the amide solvate with an aqueous base comprising sodium ions under conditions suitable for forming the compound of formula I. In a particular embodiment, the compound of formula I is a hydrate, such as a hexahydrate.

In some embodiments, the acid solvate of the compound of formula II is a carboxylic acid. In some embodiments, the carboxylic acid is $R^1COOH$ wherein $R^1$ is —H or a $C_1$-$C_4$ alkyl optionally substituted with up to three halo substituents.

In another aspect the invention comprises the novel amide solvate intermediates used in the processes described herein. For example, the disclosed compounds include an amide solvate of formula IIa:

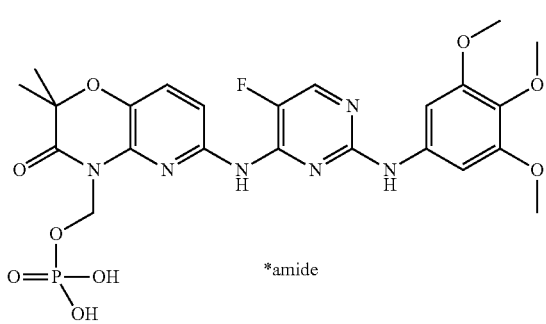

With reference to formula IIa, the amide solvate is not limited to the monosolvate, but may include solvates of multiple and non-integer numbers of amide molecules per molecule of compound II, such as, 0.5, 1, 2, and 3.

In some embodiments, the amide is a secondary amide or a tertiary amide.

In some embodiments, the amide is $R^{30}CON(R^2)_2$ where each $R^2$ is independently —H or $C_1$-$C_4$ alkyl or both $R^2$ together with the nitrogen to which they are attached form a 4 to 6 membered aliphatic ring, and $R^{30}$ is —H or $C_1$-$C_4$ alkyl; or $R^{30}$ and one of the $R^2$ together with the carbon and nitrogen to which they are attached, respectively, combine to form a 4 to 6-membered aliphatic ring and the other $R^2$ is independently —H or $C_1$-$C_4$ alkyl. In some embodiments, the amide is selected from the group consisting of a N,N-dialkylformamide, N,N-dialkylacetamide, N-alkylpyrrolidinone and N-alkylpiperidone.

In some embodiments, the amide is selected from the group consisting of a N,N-dialkylformamide, N,N-dialkylacetamide, N-alkylpyrrolidinone and N-alkylpiperidone. In some embodiments, the amide is N,N-dimethylformamide (DMF):

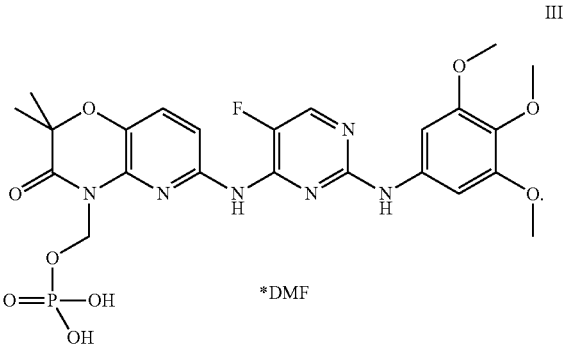 [SMILES: COc1cc(Nc2ncc(F)c(Nc3ccc4c(n3)N(COP(=O)(O)O)C(=O)C(C)(C)O4)n2)cc(OC)c1OC]

The amide solvate IIa can be synthesized by conversion of an acid solvate of the compound for formula II to the amide solvate IIa. One of ordinary skill in the art will recognize in view of the present disclosure that the amide solvates of formula IIa can be made via other forms of II, not only acid solvates of II. In some embodiments, the amide is the N,N-dialkylformamide and the conditions suitable for forming the amide solvate of the compound of formula II comprise contacting the acid solvate with the tertiary amide at a temperature of between about 20° C. and about 50° C. In some embodiments, the amide is N,N-dimethylformamide (DMF) and the conditions suitable for forming the amide solvate comprise re-slurrying the acid solvate in the DMF at a temperature of about 40° C.

In some embodiments, the aqueous base in step b) above comprises sodium hydroxide (NaOH) and an alcohol, and the conditions suitable for forming the compound of formula I comprise a temperature of between about 40° C. about 80° C. and a pH of about 9 to about 10.5. In some embodiments, the alcohol includes, but is not limited to, methanol, ethanol, iso-propanol, butanol, t-butanol, pentanol.

In some embodiments, the aqueous base in step b) above comprises sodium hydroxide (NaOH) and isopropyl alcohol (IPA), and the conditions suitable for forming the compound of formula I comprise a temperature of about 80° C. and a pH of about 10.2.

In another aspect, the invention comprises a process for preparing a precursor (VI) of the compound of formula I:

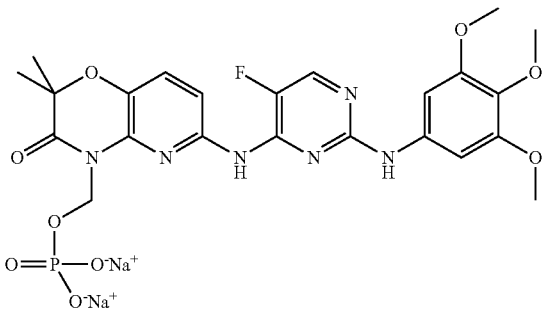

comprising contacting a compound of formula IV:

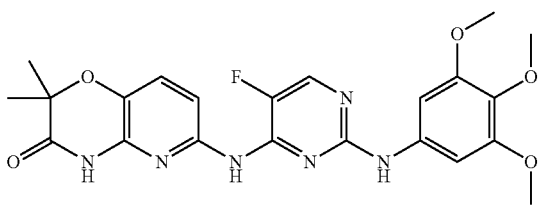

with a compound of formula V:

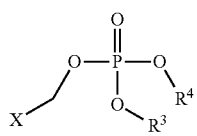

in the presence of an amide,
wherein:
$R^3$ and $R^4$ are each independently $C_1$-$C_6$ alkyl; and
X is halogen or —$OSO_2R^{62}$, where $R^{62}$ is alkyl optionally substituted with halogen (e.g., perfluorinated alkyl groups) or aryl optionally substituted with alkyl or an electron withdrawing group, e.g. halogen, $NO_2$, —CN and the like (preferably X is halogen);
under conditions suitable for forming a compound of formula VI:

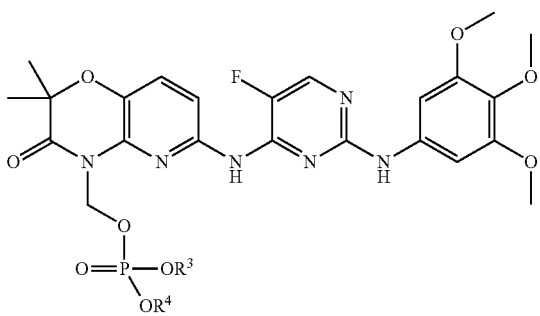

In another embodiment, the invention comprises a method of converting the precursor VI into the compound of formula I, the method comprising:
a) contacting the compound of formula VI with an acid under conditions suitable for forming an acid solvate of a compound of formula II:

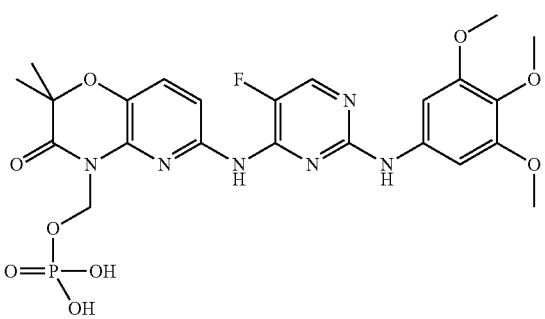

b) contacting the acid solvate of the compound of formula II with an amide under conditions suitable for forming an amide solvate of the compound of formula II; and c) contacting the amide solvate of the compound of formula II with an aqueous base comprising sodium ions under conditions suitable for forming the compound of formula I.

In a particular embodiment, the compound of formula I produced by this method is a hydrate, such as a hexahydrate.

In another embodiment, the invention comprises the sequential combination of the two previous methods (i.e., a method comprising the method of making precursor VI followed by the method of converting VI to the compound of formula I).

In a more generic sense, the invention is directed to making the compound of formula I by: reacting compounds IV and V to give compound VI; converting compound VI to compound II, or an acid solvate of II; converting compound II, and/or its acid solvate, to compound IIa, the amide solvate; and converting compound IIa to compound I (optionally in the form of a hydrate, such as a hexahydrate).

In some embodiments, the compound of formula V is di-tert-butyl chloromethyl phosphate:

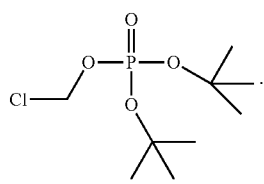

The conditions suitable for producing the compound of formula VI can comprise:
(i) combining the compound of formula IV with the compound of formula V with a base in a polar solvent; and
(ii) washing the product obtained from step (i) in an aqueous base solution.

Examples of bases suitable for use in steps (i), (ii) or both include, but are not limited to, carbonates, such as cesium carbonate, sodium carbonate, sodium bicarbonate, potassium carbonate, hydroxides, such as, sodium hydroxide, potassium hydroxide, lithium hydroxide, and 1°, 2° and 3° amines such as triethylamine, N,N-dimethylaniline, N,N-diethylaniline and ammonia, as well as metal alkoxides e.g. potassium t-butoxide.

Examples of polar solvent include, but are not limited to, N,N-dimethylformamide (DMF), N,N-dimethylacetamide, tetrahydrofuran, dichloromethane, acetone, acetonitrile, dimethylsulfoxide. Mixtures of such solvents also can be used as is known to those of skill in the art. Moreover, those of skill in the art also would understand that such polar solvents can include non-polar components in a mixture with one or more polar solvents so long as the resultant solvent mixture is polar. Solvents typically considered to be polar include those having a dielectric constant, E, of at least about 5 and typically greater than about 7 or 8. For example, tetrahydrofuran has a dielectric constant, E of 7.6, whereas DMF has a dielectric constant of 37.

In some embodiments, the base in step (i) above comprises at least one of cesium carbonate ($Cs_2CO_3$) and potassium carbonate ($K_2CO_3$); the polar solvent comprises at least one of DMF and N,N-dimethylacetamide (DMAc); and the aqueous base in step (ii) above comprises at least one of sodium bicarbonate ($NaHCO_3$) and sodium hydroxide (NaOH).

In some embodiments, the compound of formula VI is not isolated.

In some embodiments, the compound of formula V is stabilized with N,N-dimethylacetamide (DMAc) solvent.

Generally, the compound of formula V, such as, di-tert-butyl chloromethyl phosphate, is an unstable product. As an example, di-tert-butyl chloromethyl phosphate undergoes decomposition upon storage to give off heat and iso-butene gas. With reference to the scheme below, and while not intending to be bound by theory, it is believed that the presence of trace amounts of acid catalyzes the cleavage of an O-tert-butyl group on di-tert-butyl chloromethyl phosphate A to give mono-text-butyl species C with the release of isobutene. Species C can act as an acid source further driving autocatalytic decomposition to phosphate E. As indicated by the dotted line in the scheme below, phosphate E can also provide protons to feed into the autocatalytic decomposition of A. Decomposition of A is exothermic and produces two moles of isobutene per mole of A.

of the sample corresponds to acid E as depicted above. Further tests have shown the pressure increase due to isobutene release can be as great as 80 bar. Also, isobutene is a flammable gas therefore venting large quantities of iso-butene can be dangerous.

Therefore, it is normally critical to design equipment for the storage of the compound of formula V that can withstand the pressure build up. Various other safety measures need to be taken as well, such as temperature control, distillation time, and safety valve dimension, to avoid equipment damage during the unwanted decomposition reaction.

However, it was unexpectedly found that the addition of N,N-dimethylacetamide (DMAc) stabilizes di-tert-butyl chloromethyl phosphate such that the compound may be stored at about 60° C. with no autocatalytic decomposition

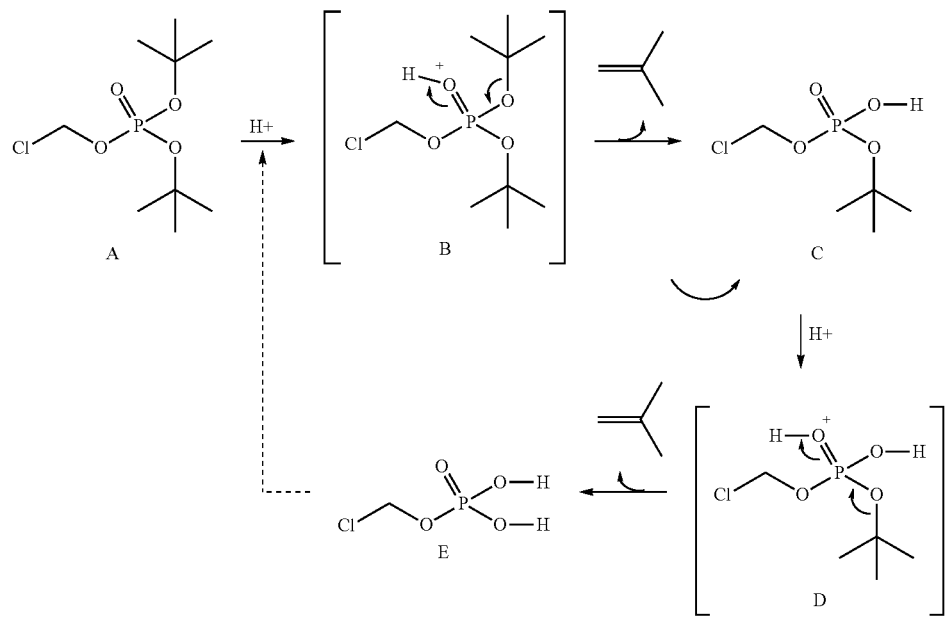

Figure 2:
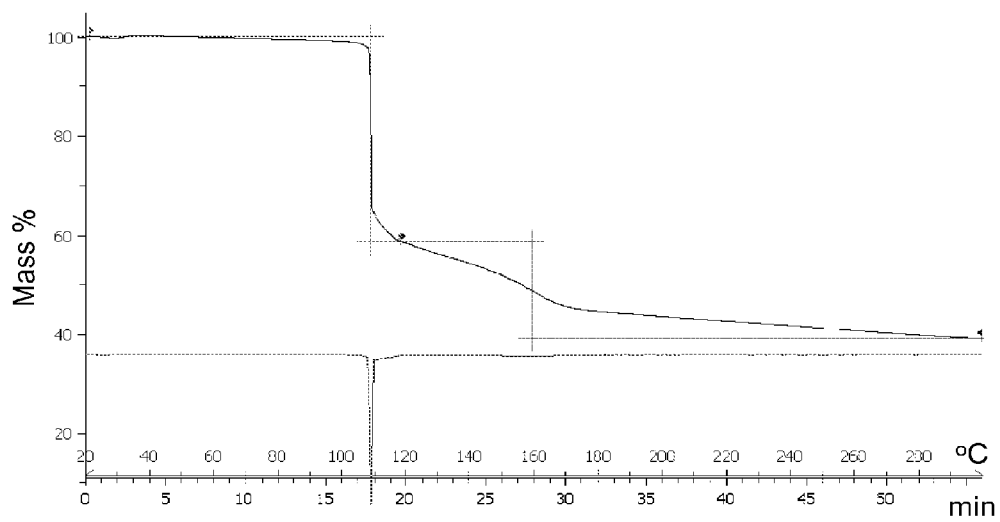
FIG. 2 illustrates a Thermo-Graphic-Analysis (TGA) experiment with neat di-tert-butylchloromethyl phosphate (7.7 mg).
Figure 3:
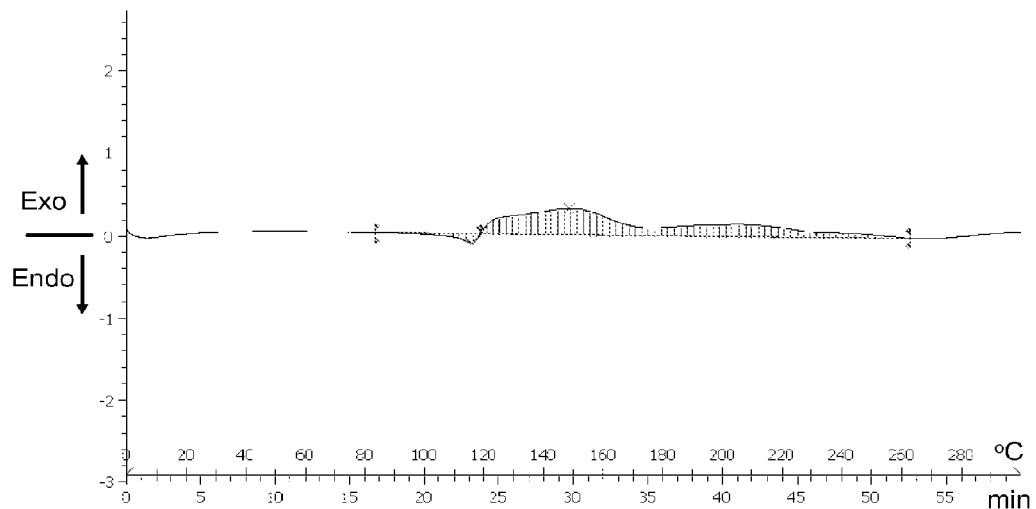
FIG. 3 illustrates a dynamic differential scanning calorimetry experiment in closed cup of a 36% solution of di-tert-butylchloromethyl phosphate (5.6 mg) in DMAc.
Figure 4:
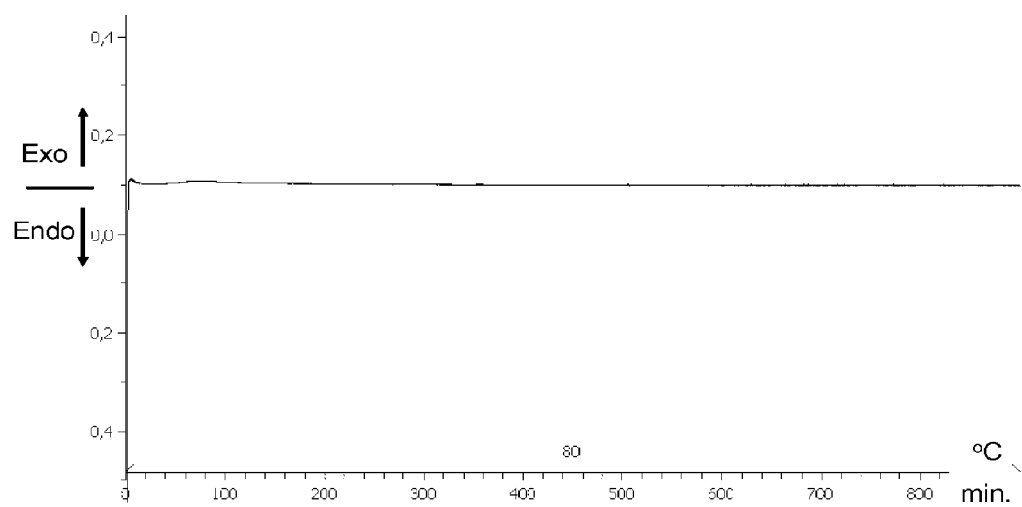
FIG. 4 illustrates a isotherm differential scanning calorimetry experiment in closed cup of a 36% di-tert-butylchloromethyl phosphate (10.9 mg) solution in DMAc at 80° C.

When stored under adiabatic conditions, the heat and pressure build-up from decomposition can be significant. FIG. 1 illustrates that storage of di-tert-butyl chloromethyl phosphate under adiabatic conditions can result in decomposition whereby the pressure and temperature increase dramatically. FIG. 1 illustrates a dynamic differential scanning calorimetry experiment (DSC) in closed cup of neat di-tert-butylchloromethyl phosphate (heating from 0° C. to 300° C. at a rate of 5° C./min under a $N_2$ flow of 50 mL/min.). Referring to FIG. 1, after an endothermic signal (start of isobutene release under upon formation of acidic by products; extrapolated peak at 99.10° C. with a peak width of 0.33° C. and an integrated area of –108.45 mJ) a very sharp exothermic signal at about 100° C. is observable (extrapolated peak at 100.57° C. with a peak width of 3.99° C. and a integrated area of 2717.05 mJ), which is typical for an autocatalytic decomposition. FIG. 2 illustrates a Thermo-Graphic-Analysis (TGA) experiment with neat di-tert-butylchloromethyl phosphate, showing that continuous decomposition is observed with isobutene offgassing. In FIG. 2, the sample was heated from 20° C. to 300° C. at a rate of 5° C./min under $N_2$ at a flow rate of 80 mL/min. The sample showed a 41.465% (3.189 mg) mass loss between about 21° C. and 119° C.; and a 19.526% (1.502 mg) mass loss between about 119° C. and 300° C. Most of the isobutene is sharply split off at 110° C.; after 1 h at 300° C. the weight and no gas being formed (see FIGS. 3-4). FIG. 3 illustrates a dynamic differential scanning calorimetry experiment in closed cup of a 36% solution of di-tert-butylchloromethyl phosphate in DMAc (heating from 0° C. to 300° C. at a rate of 5° C./min. under a $N_2$ flow of 50 mL/min.). After an endothermic signal (some isobutene loss due to trace acid; extrapolated peak at 116.42° C. with a peak width of 6.19° C. and an integrated area of –70.78 mJ) a smooth exothermic signal at 120° C. is observable (no sharp exothermic signal at 99 to 100° C. is observable; extrapolated peak at 129.74° C. with a peak width of 42.52° C. and an integrated area of 1362.40 mJ). This indicates that the system is not undergoing autocatalytic decomposition. FIG. 4 illustrates an isothermic differential scanning calorimetry (DSC) experiment in closed cup of a 36% di-tert-butylchloromethyl phosphate solution in DMAc at 80° C. (under a $N_2$ flow of 50 mL/min.). No endothermic or exothermic decomposition of a 36% di-tert-butylchloromethyl phosphate solution in DMAc is observed at storage temperatures (45, 60 and even 80° C.) over 15 hours, thus the di-tert-butylchloromethyl phosphate is stabilized. In fact, isothermal heating at 60° C. of a solution from 68.7 g of a 36% solution of di-tert-butylchloromethyl phosphate in DMAc for over 96 hours generated no gas (isobutene).

It is to be understood that any amide, such as, but not limited to, DMAc, may be used to stabilize the compound of formula V, including di-tert-butyl chloromethyl phosphate. Such amides are well known to a person of ordinary skill in the art. Examples of such amides include, but are not limited to, N,N-dimethylacetamide, N,N-dimethylformamide, N-methylpyrrolidinone. In some embodiments, a solvent may be optionally added to a combination of the amide and di-tert-butyl chloromethyl phosphate. In some embodiments, the amide may also be a solvent. For example, DMAc can be used as the amide as well as the solvent.

Accordingly, in one aspect, there is provided a composition comprising di-tert-butyl chloromethyl phosphate:

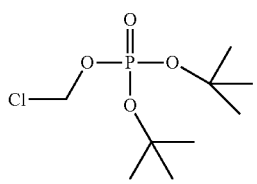

and an amide optionally in a solvent.

In some embodiments, the amide is also the solvent.
In some embodiments, the amide is a tertiary amide.
In some embodiments, the tertiary amide is N,N-dimethylacetamide (DMAc).

The improved process for the synthesis of the compound of formula I is as illustrated in Schemes I-VII below.

3. Synthetic Schemes

Starting materials used in the synthesis described herein are available commercially. The synthesis of the compound of formula V is as shown in Scheme I below:

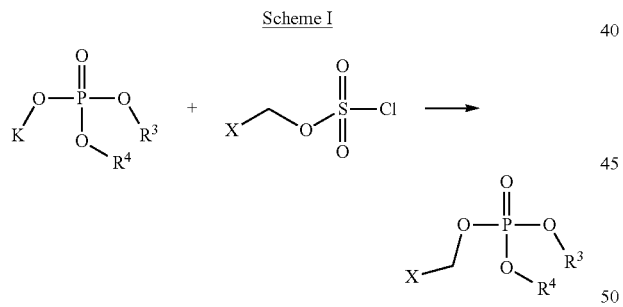

Scheme I

According to Scheme I, compound of formula V is obtained by the reaction of potassium dialkyl phosphate group ($R^3$ and $R^4$ as defined hereinabove) with an alkylating agent (X as defined hereinabove), such as a halomethylchlorosulfate in the presence of a phase transfer catalyst (PTC). Numerous examples of phase transfer catalysts are known to those of skill in the art. Examples of such phase transfer catalysts include, without limitation tetraalkyl ammonium salts, such as tetrabutyl ammonium salts. For example, di-tert-butyl chloromethyl phosphate can be obtained by the reaction of potassium or sodium di-tert-butyl phosphate (PDP) with chloromethylchlorosulfate (CMCS) in the presence of tetrabutylamonium bisulfate (TBAHS).

Scheme Ia below (as well as FIGS. 1-4 and the Examples below), shows that the pH adjustment and the addition of N,N-dimethylacctamide (DMAc) stabilizes di-tert-butyl chloromethyl phosphate such that the compound may be kept at about 60° C. with no gas being formed.

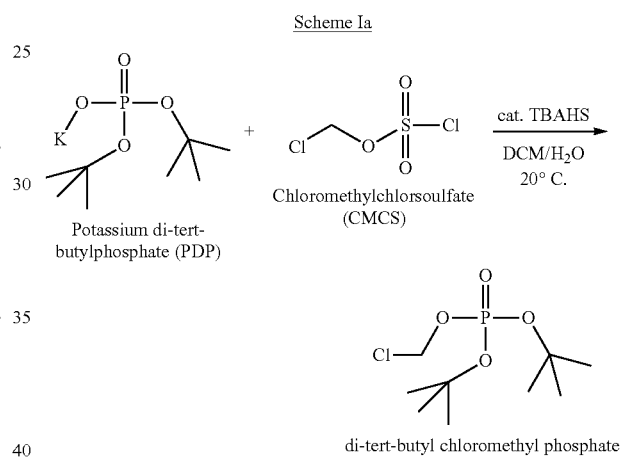

Scheme Ia

It is to be understood that the synthesis of di-tert-butyl chloromethyl phosphate in Scheme Ia is for illustration purposes only. Synthesis of other phosphates of the compound of formula V by following Scheme Ia can be carried out by routine adaptation of the method. In addition, sodium or other salts of di-tert-butyl phosphate and other reaction conditions can be used to make di-tert-butyl chloromethyl phosphate.

The synthesis of the compound of formula VIa from compound of formula IV is as illustrated in Scheme II below:

Scheme II

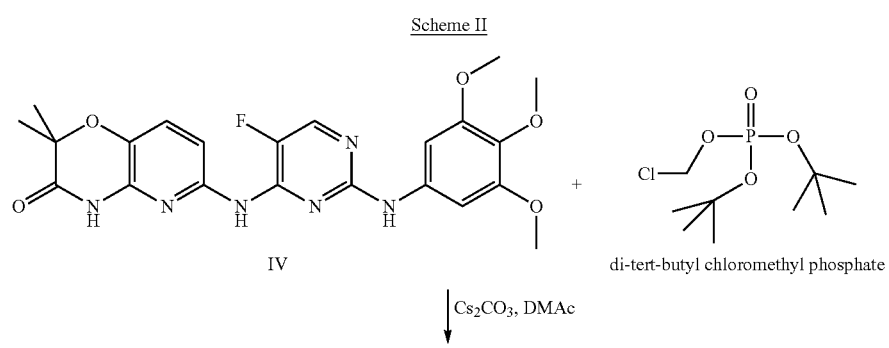

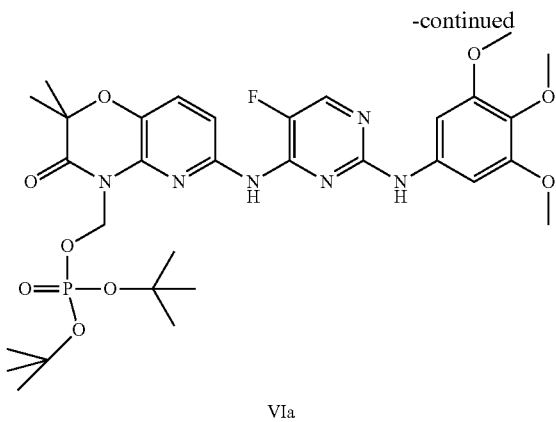

VIa

According to Scheme II, the compound of formula IV is treated with di-tert-butyl chloromethyl phosphate to result in the compound of formula VIa (such as step B of Example 1 herein). It is to be understood that reaction of a compound of formula IV with di-tert-butyl chloromethyl phosphate is for illustration purposes only. Other phosphates, such as compound of formula V described herein, may be reacted with the compound of formula IV to result in the compound of formula VI using routine adaptation of the method. The steps described further below for the compound of formula VIa may also be applied to the compound of formula VI.

In some embodiments, $Cs_2CO_3$ as a base and DMAc as the solvent in the synthesis of the compound of formula VIa. Base $Cs_2CO_3$ may be substituted with $K_2CO_3$ or KOtBu, each alone or in combination with each other or $Cs_2CO_3$. The compound of formula VIa can be isolated as a solid but can also be obtained as solution in methyl tert-butyl ether (MtBE).

Synthesis of the acid solvate of the compound of formula II from a compound of formula VIa is as illustrated in Scheme III and exemplified in step C of Example 1 below:

Scheme III

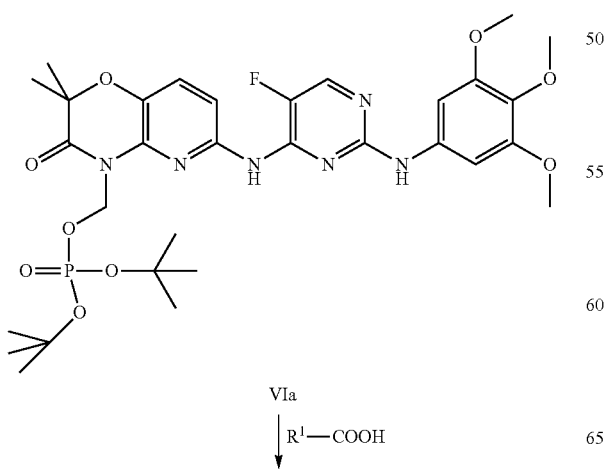

VIa

↓ $R^1$—COOH

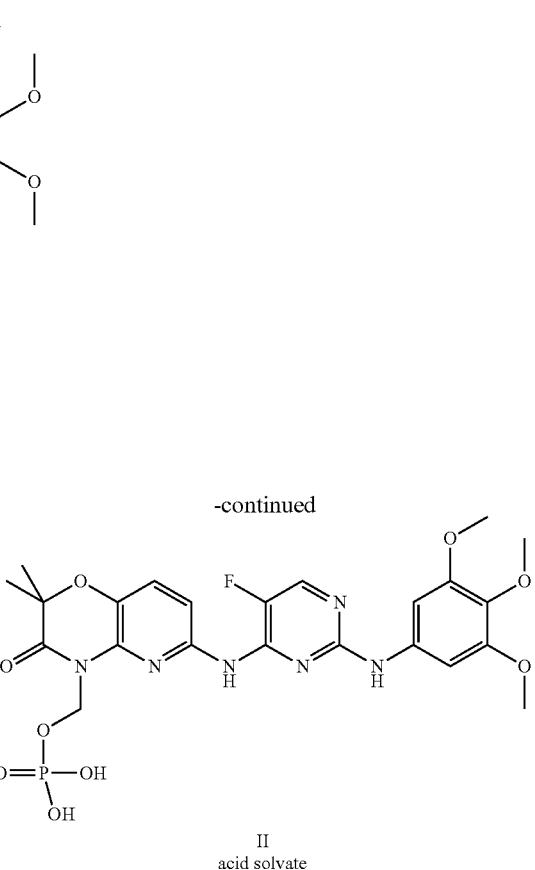

II
acid solvate

According to Scheme III, the compound of formula VIa is dissolved in a mixture of an acid $R^1$—COOH($R^1$ is as defined hereinabove) and water and heated to about 55-70° C. For example, as described in step C of Example 1, the compound of formula VIa is dissolved in acetic acid and water (4:1 AcOH:$H_2O$) and heated to 67° C. to yield an acetic acid solvate of the compound of formula II.

The synthesis of the amide solvate of the compound of formula II from the acid solvate of the compound of formula II is as illustrated in Scheme IV and exemplified in step C of Example 1:

Scheme IV

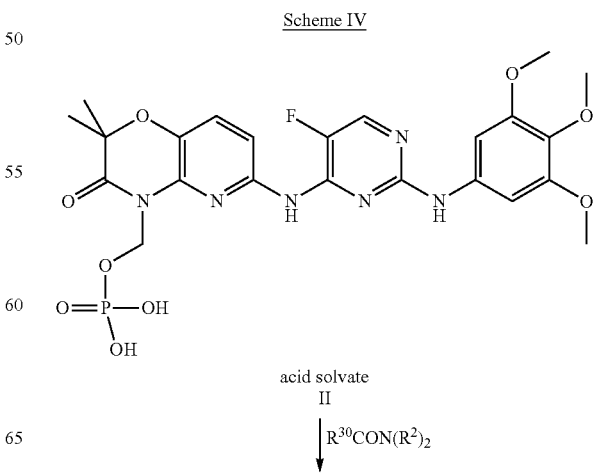

acid solvate
II

↓ $R^{30}CON(R^2)_2$

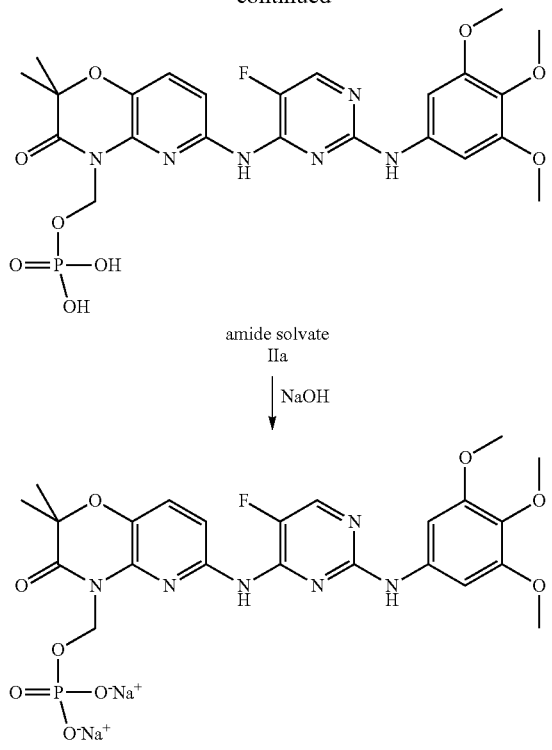

wherein the compound of formula I is optionally in the form of a hydrate, such as a hexahydrate.

The conversion of the acid solvate of the compound of formula II to the amide solvate of the compound of formula II comprises reslurrying the acid solvate of the compound of formula II in a tertiary amide, such as $R^{30}CON(R^2)_2$ (where $R^2$ and $R^{30}$ are as defined hereinabove) between about 20° C.-50° C. For example, as described in step C of Example 1, the acetic acid solvate of the compound of formula II is reslurried in DMF at about 40° C. to yield a DMF solvate of the compound of formula II.

This step of reslurrying of the acid solvate to obtain the DMF solvate of the compound of formula II results in a higher quality product with less starting material and by-products, such as, depletion of the compound of formula IV to <1 mole % and of p-dimer to <0.1 mole %. The product is stable at 40° C. for about 24 h. This improved process results in improved filterability of the product. This improved process further results in increased yield by about 10%.

A synthesis of the compound of formula I from the amide solvate of the compound of formula II is as exemplified in step D of Example 1. The amide solvate of the compound of formula II is taken in an alcohol, such as, isopropylalcohol/water where the pH is adjusted between about 9 to about 10.5 by adding a base, such as, NaOH. The solution is heated between about 40° C. to about 80° C. In one embodiment, the DMF solvate of the compound of formula II is treated with isopropylalcohol/water at a temperature of about 80° C. and a pH of about 8-10.2 to result in the compound of formula I.

IV. EXAMPLES

The invention is further understood by reference to the following examples, which are intended to be purely exemplary of certain aspects of the invention and are not intended to limit the scope.

In the examples below as well as throughout the application, the following abbreviations have the following meanings. If not defined, the terms have their generally accepted meanings.

cm=centimeter
CMCS=chloromethylchlorsulfate
$Cs_2CO_3$=cesium carbonate
DCM=dichloromethane
DMAc=dimethylacetamide
h=hours
HCl=hydrochloric acid
IPA=isopropylalcohol
mbar=millibar
MeOH=methanol
MtBE=methyl-tert-butyl ether
mol=molar
mL=milliliter
g=gram
mg=milligram
rpm=revolutions per minute
min=minute
mm=millimeter
N=normal
$Na_2CO_3$=sodium carbonate
$NaHCO_3$=sodium bicarbonate
NaOH=sodium hydroxide
NMP=N-methylpyrrolidinone
NMR=nuclear magnetic resonance
PDP=di-t-butylphosphate
PTC=phase transfer catalyst
TBAHS=tetrabutylamoniumhydrogehsulfate
v/v=volume/volume
° C.=degree Celsius
$POCl_3$=Phosphorus oxychloride

Example 1

A. Preparation of di-tert-butyl chloromethyl phosphate

Procedure I

Preparation of stabilized di-tert-butyl chloromethyl phosphate

Preparation of di-tert-butyl chloromethyl phosphate, has been described in the literature, such as in Mantyla, et al. *Tetrahedron Letters*, 43 (2002), 3793-3794 and Chadwick, et al. U.S. 2006/0047135. We have found improvements to these processes whereby the yield is increased, with high purity, and the di-tert-butyl chloromethyl phosphate is stabilized via exposure to an amide. The specific example below illustrates this aspect of the invention.

Surprisingly, it was found that di-tert-butyl chloromethyl phosphate could be synthesized in excellent yield (>90%) and purity (>99%) by dosing 2.5 eq. CMCS to a two phase mixture of PDP and phase transfer catalyst TBAHS in DCM/water and adjusting pH value to 8 at the same time by addition of 20% aqueous NaOH. Additionally it was found, that the stability of di-text-butyl chloromethyl phosphate was tremendously enhanced and no auto catalytic decomposition behaviour was observed by preparation of a 30 w % solution in dimethylacetamide (DMAc).

Description of the Process:

Di-tert-butyl chloromethyl phosphate was synthesized using a TBAHS phase transfer catalysed reaction of PDP in DCM/H₂O with 2.5 eq. CMCS at 18° C. The pH was monitored and adjusted to 8 by addition of 20% aqueous NaOH.

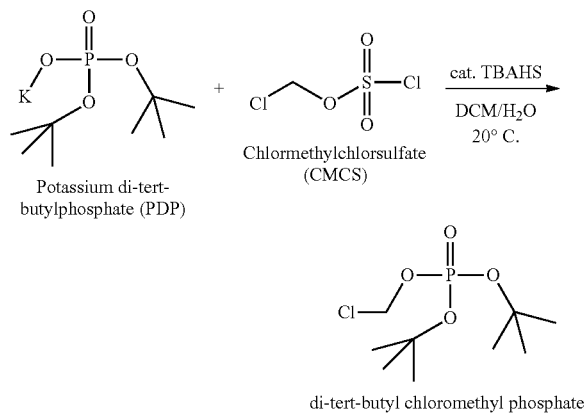

Potassium di-tert-butylphosphate (PDP)

Chlormethylchlorsulfate (CMCS)

di-tert-butyl chloromethyl phosphate

The DCM was removed at 20° C. and a pH>7 at reduced pressure (recycling of DCM). To the crude di-tert-butyl chloromethyl phosphate was added MtBE, and the TBASHS was removed by washing the MtBE layer with 2% aqueous bicarbonate solution. To stabilize the di-tert-butyl chloromethyl phosphate, DMAc was added, and then the MtBE was distilled off. The yield was >90% based on PDP starting material. The purity of di-tert-butyl chloromethyl phosphate in DMAc according to ¹H-NMR>99%

This procedure has at least the following advantages: 1) a liquid base (aqueous NaOH) instead of an excess of solid base such as NaHCO₃, Na₂HPO₄ or Na₂CO₃ can be used; 2) the reaction can be performed in a more concentrated state because an excess of less soluble bicarbonates or phosphates are replaced by soluble chlorides, thereby minimizing volume requirements and reaction time while improving yield. Also, the stability of the di-tert-butyl chloromethyl phosphate is enhanced, up to 40° C., by preparation of, for example, a 30 w % solution in DMAc.

In a specific example, 56.3 g of PDP (1.0 mol equivalent: 91.2 w %) was mixed with 3.53 g of TBAHS (0.05 eq.), 60 g of water and 300 g of DCM. At room temperature, 86.6 g of CMCS (2.5 eq.) was dosed to the reaction mixture over 4 h. During the dosing of CMCS, the pH was adjusted to 8 by addition of 227 g of 20% aqueous NaOH. The resulting two phase reaction mixture was stirred overnight at 20° C. The DCM was distilled off at 20° C. under reduced pressure (500→300 mbar) from the two phase mixture. After addition of 200 mL MtBE to the residue, layers were separated. The water layer was discarded and the organic layer was washed once with 300 mL 2% aqueous NaHCO₃ to remove phase transfer catalyst. After addition of 90 mL DMAc, MtBE was distilled off at 40° C. and reduced pressure. Liquid nitrogen was bubbled through the resulting mixture for 1 hour to remove traces of DCM and MtBE. The di-tert-butyl chloromethyl phosphate (128 g of an oil) was obtained and analysed by ¹H-NMR, showing a yield of di-tert-butyl chloromethyl phosphate of 90.7%. (di-tert-butyl chloromethyl phosphate: 36.4%; DMAc: 63.4 w %; DCM: 0.03 w %; MtBE: 0.01 w %; PTC: 0.01 w %; Water: 0.6 w %).

Additional advantages include: 1) DCM can be recycled, 2) PTC can be removed in a single extraction, 3) only 5 mol % of PTC is needed, and 4) all but minute traces of DCM and MtBE are remove by bubbling N₂.

B. Preparation of Compound of Formula VIa in MtBE

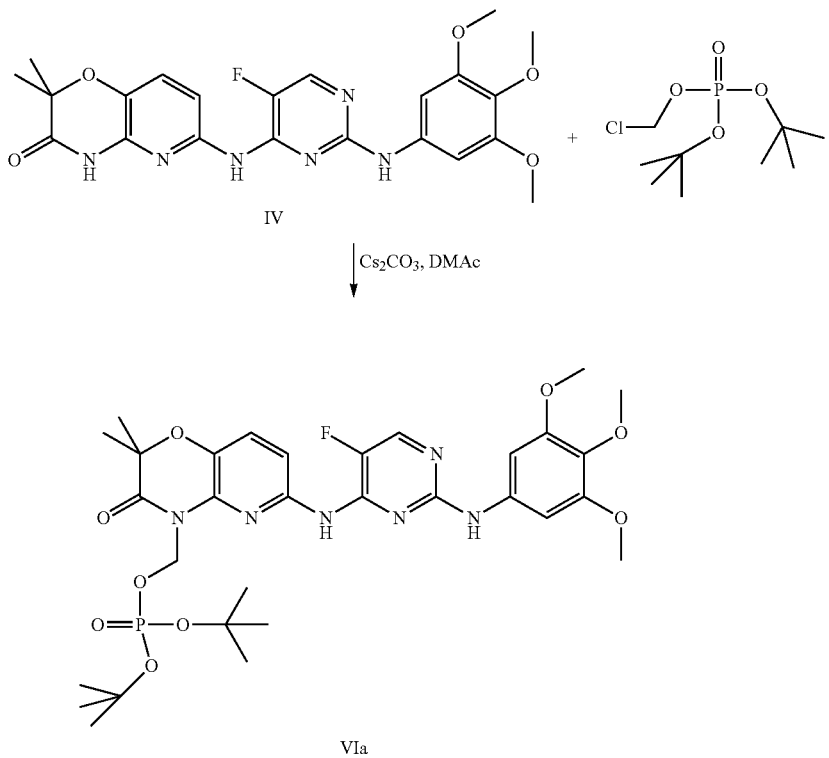

Description of Synthesis of Compound of Formula VIa:

Cesium carbonate, 27.3 g (1.2 eq.), 185 g of N,N-Dimethylacetamide, 33.5 g of compound of formula IV (1 eq., 70 mmol) and 74 g of 30.6 w % di-tert-butyl chloromethyl phosphate (1.25 eq.) in DMAc were charged and stirred at 40° C. overnight. A beige suspension resulted. The suspension was cooled to room temperature and 118 mL each of MTBE and water were added. The phases were separated and the aqueous layer washed with 94 mL MTBE. The organic layers were each washed with 94 mL water. The organic layers yielded 187.9 g of compound VIa in MTBE, (yield 74% based on 70 mmol compound of formula IV).

C. Preparation of Compound of Formula IIa (Amide Solvate)

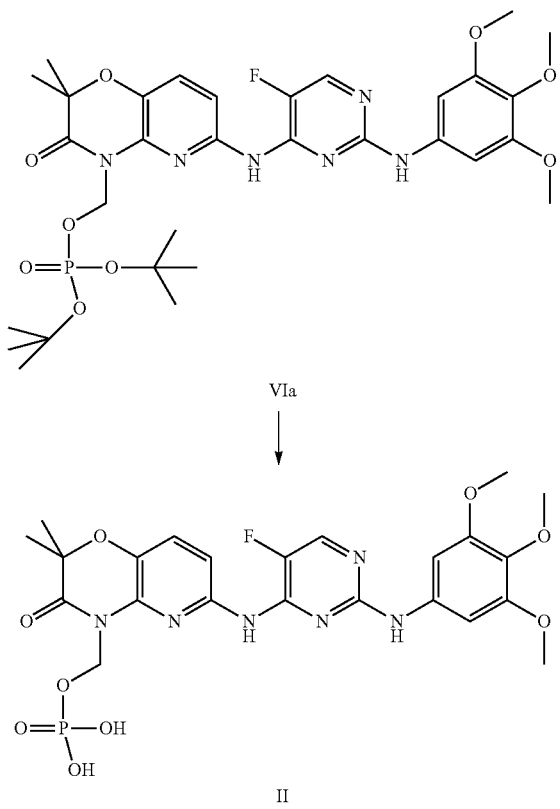

Description:

Acetic acid (168.6 g, 160.6 mL) was combined with an equal amount of water and the mixture heated to 67° C. The compound of formula VIa (187 g, 170 mL) of the solution in MTBE obtained as described above was added to the aqueous acetic acid. Most of the MTBE was distilled off at atmospheric pressure and the resulting solution stirred for 2 h, resulting in a yellow suspension. The remaining MTBE was distilled off at 300 mbar and the suspension cooled to 20° C. and filtered to give an off-white solid. The filter cake was washed with cold acetone (2×160 mL) and dried overnight at 30° C. to yield 29.8 g of the compound of formula II as an acetic acid solvate.

A suspension of 29.8 g of the compound of formula II as an acetic acid solvate at or about 1:1 stoichiometry) and 150 mL DMF were heated to 50° C. and stirred for 2 h. The suspension was then cooled to room temperature and filtered. The filter cake was washed three times with 98 mL of MTBE and dried under vacuum overnight at 30° C. The amide solvate of the compound of formula II (26.7 g) was obtained (yield 55% based on 70 mmol of compound IV).

D. Preparation of a Hexahydrate of the Compound of Formula I

The amide solvate (10 g, 15 mmol) was suspended in 100 mL water and stirred for 1 hour. Subsequently, 50 mL IPA were added and the pH was adjusted from 3.3 to 8.5 by addition of 31.9 g of 1M NaOH. The reaction mixture was heated to 82° C., stirred for 1 hour, filtered through a 10 micron filter, cooled to 20° C., and stirred over night. The resulting suspension was filtered and the filter cake washed twice with 40 mL acetone and dried under vacuum over night at 40° C. to give 8.6 g of a hexahydrate of the compound of formula I (77% yield).

What is claimed is:

1. A composition comprising di-tert-butyl chloromethyl phosphate:

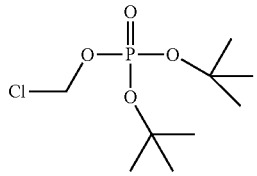

and an amide, wherein
the amide is of formula $R^{20}CON(R^{21})_2$
$R^{20}$ is selected from hydrogen or optionally substituted alkyl; and
each $R^{21}$ is independently hydrogen or optionally substituted alkyl, or both of $R^{21}$ and the nitrogen with which they are attached form a 4 to 6 membered aliphatic ring;
or
$R^{20}$ and one of the $R^{21}$ join together with the carbon and nitrogen to which they are attached, respectively, to form a 4 to 6 membered nitrogen containing ring, and the other $R^{21}$ is hydrogen or optionally substituted alkyl;
and the optional substituents are selected from alkyl, halo, haloalkyl, nitroso, and cyano.

2. The composition of claim 1, wherein the amide is a solvent.

3. The composition of claim 2, wherein the amide is a tertiary amide.

4. The composition of claim 3 wherein the tertiary amide is N,N-dimethylacetamide (DMAc).

* * * * *

UNITED STATES PATENT AND TRADEMARK OFFICE
CERTIFICATE OF CORRECTION

Page 1 of 1

PATENT NO. : 8,691,798 B2
APPLICATION NO. : 13/912856
DATED : April 8, 2014
INVENTOR(S) : Ulfried Felfer et al.

It is certified that error appears in the above-identified patent and that said Letters Patent is hereby corrected as shown below:

Title page, item (12), delete "Feifer et al." and replace with:

-- Felfer et al. --.

Title page, item (72) Inventors, delete "Ulfried Feifer" and replace with:

-- Ulfried Felfer --.

Signed and Sealed this
Fourteenth Day of April, 2015

Michelle K. Lee
*Director of the United States Patent and Trademark Office*